(12) United States Patent
Hsu

(10) Patent No.: US 9,823,584 B2
(45) Date of Patent: Nov. 21, 2017

(54) METHOD FOR FABRICATING ELECTROCHEMICAL SENSING TEST PIECE

(71) Applicant: CHEESHIN TECHNOLOGY CO., LTD., Miaoli County (TW)

(72) Inventor: Kuo-Chen Hsu, Miaoli County (TW)

(73) Assignee: Cheeshin Technology Co., Ltd., Maioli County (TW)

( * ) Notice: Subject to any disclaimer, the term of this patent is extended or adjusted under 35 U.S.C. 154(b) by 50 days.

(21) Appl. No.: 15/007,577

(22) Filed: Jan. 27, 2016

(65) Prior Publication Data

US 2017/0131639 A1 May 11, 2017

(30) Foreign Application Priority Data

Nov. 11, 2015 (TW) .............................. 104137252 A

(51) Int. Cl.
*G03F 7/20* (2006.01)
*H01L 39/24* (2006.01)
*G01N 27/26* (2006.01)
*G01N 27/327* (2006.01)

(52) U.S. Cl.
CPC ......... *G03F 7/70416* (2013.01); *G01N 27/26* (2013.01); *G01N 27/3271* (2013.01); *H01L 39/2467* (2013.01)

(58) Field of Classification Search
CPC .. G01N 27/26; G01N 27/327; G01N 27/3271; H01L 39/2467

USPC .................................... 216/13, 18, 39, 77, 78
See application file for complete search history.

(56) References Cited

U.S. PATENT DOCUMENTS

| | | | |
|---|---|---|---|
| 2010/0200538 A1* | 8/2010 | Petisce ................. | A61B 5/0006 216/13 |
| 2014/0166612 A1* | 6/2014 | Petisce ................. | A61B 5/0006 216/13 |
| 2014/0284304 A1 | 9/2014 | Chen | |
| 2015/0276651 A1* | 10/2015 | Petisce ............... | G01N 27/3272 204/403.1 |
| 2016/0116429 A1* | 4/2016 | Murase ................. | C12Q 1/006 204/415 |
| 2016/0341688 A1* | 11/2016 | Lim ....................... | G01N 33/50 |

* cited by examiner

*Primary Examiner* — Binh X Tran
(74) *Attorney, Agent, or Firm* — Muncy, Geissler, Olds & Lowe, P.C.

(57) ABSTRACT

A method for fabricating an electrochemical sensing test piece comprises steps: forming an electrode layer on a substrate; etching the electrode layer to reduce the area of the electrode layer to be smaller than the area of the substrate, wherein the electrode layer has a test zone and a reading zone neighboring the test zone; forming an insulation member surrounding the test zone and covering the perimeter of the test zone; forming an enzyme layer on the test zone; and forming an insulation layer on the enzyme layer and the periphery of the reading zone and fabricating the insulation layer to have an opening revealing a portion of the enzyme layer. The insulation member fixes the effective reaction area of the tested material and increases measurement accuracy.

9 Claims, 11 Drawing Sheets ns test piece.

METHOD FOR FABRICATING ELECTROCHEMICAL SENSING TEST PIECE

FIELD OF THE INVENTION

The present invention relates to a sensing test piece, particularly to a method for fabricating an electrochemical sensing test piece.

BACKGROUND OF THE INVENTION

With advance of medical science and technology, chronic diseases, which are hard to heal completely but likely to occur repeatedly, have been the main causes of death. Busy modern people are hard to spare their time to go to hospitals for comprehensive health examination. Therefore, many household inspection instruments are developed to monitor physiological status and assist in detecting diseases for early diagnosis, early prevention and early treatment of diseases.

A common household inspection instrument includes a test machine and test pieces for the test machine. After the tested material contacts the test piece, the test machine can undertake inspection fast. A US patent publication No. 20140284304 disclosed a "Method of Fabricating Test Strip of Biological Fluid", which comprises steps: ink-printing metal ions on a non-conductive filmed material to form a printed metal circuit; surface-treating the printed metal circuit to reveal the metal ions; chemically electroplating the revealed metal ions to form an electrode zone on the printed metal circuit; forming a sensing agent layer on the electrode zone; covering the metal circuit with a separation layer and forming an opening to reveal the sensing agent layer and the electrode zone for receiving the tested material.

In spite of reducing the cost of fabricating test pieces, the ink-printing technology generates irregular edges of the electrode (the printed metal circuit). Thus, the effective reaction area where the tested material contacts the test piece becomes indefinite, and the accuracy of test is affected. Besides, during forming the sensing agent layer, gaps are likely to appear in the lateral of the electrode zone and cause indefinite reaction area. Therefore, solving the problem of indefinite effective reaction area and promoting the accuracy of inspection will favor people very much.

SUMMARY OF THE INVENTION

The primary objective of the present invention is to overcome the problem that the conventional test piece technology cannot fix the effective reaction area and has lower inspection accuracy.

In order to achieve the abovementioned objective, the present invention proposes a method for fabricating an electrochemical sensing test piece, which comprises Step S1: forming an electrode layer on a substrate;

Step S2: etching the electrode layer to reduce the area of the electrode layer to be smaller than the substrate and form on the electrode layer a test zone and a reading zone neighboring the test zone;

Step S3: forming an insulation member surrounding the test zone and covering the perimeter of the test zone;

Step S4: forming an enzyme layer on the test zone; and

Step S5: forming an insulation layer on the enzyme layer and around the reading zone and making an opening of the insulation layer to reveal a portion of the enzyme layer.

The present invention is characterized in

1. Fixing the effective reaction area of the tested material and the test zone via covering the perimeter of the test zone with an insulation member, and thus upgrading test accuracy;
2. Preventing the lateral sides of the electrode layer from being exposed via disposing the insulation member and the insulation layer on the perimeter of the electrode layer, and thus exempting the test precision from being degraded.

DETAILED DESCRIPTION OF THE PREFERRED EMBODIMENTS

The technical contents of the present invention will be described in detail in cooperation with the drawings below.

Refer to FIG. 1 to FIG. 4F for a first embodiment. According to the first embodiment, the present invention provides a method for fabricating an electrochemical sensing test piece, which comprises the steps of S1-S5.

In the step S1, form an electrode layer 20 on a substrate 10, wherein the substrate 10 is made of a material selected from the group consisting of polyethylene terephthalate (PET), polyethylene naphthalate (PEN), cellulose triacetate, polylactic acid, and combinations thereof. In the first embodiment, the method of the present invention further comprises the step of S1A and Step S1B.

Figure 4A:
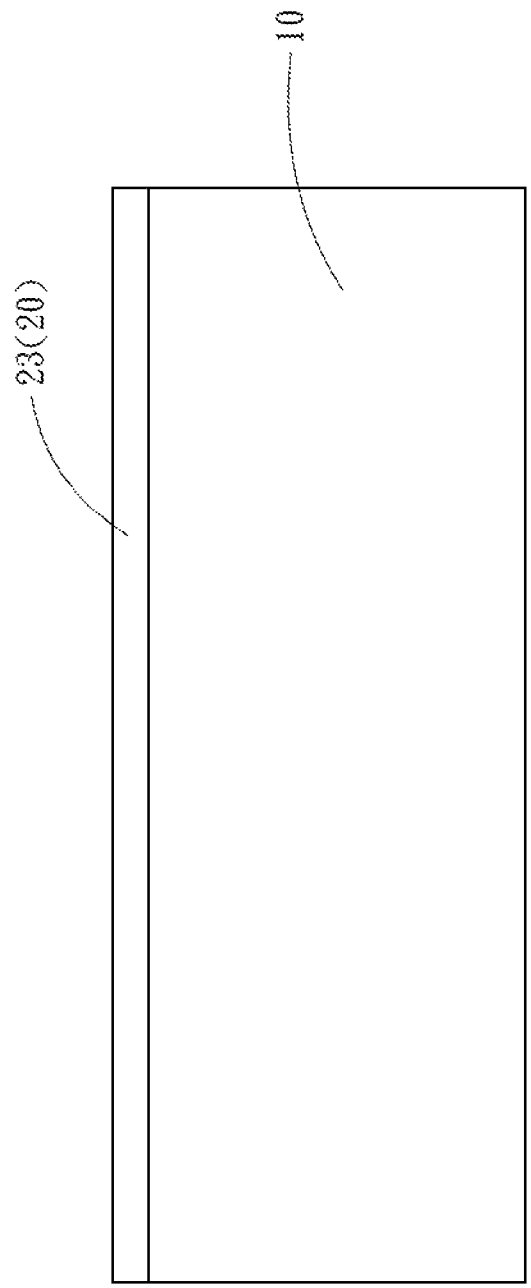
FIGS. 4A-4F are sectional views schematically showing fabrication steps according to the first embodiment of the present invention.

In the step S1A, form a first electrode layer 23 on the substrate 10, as shown in FIG. 4A, wherein the first electrode layer 23 is made of a material selected from the group consisting of titanium, copper, nickel, silver, aluminum, chromium, and combinations thereof, such like alloys, and wherein the first electrode layer 23 has a thickness of 20-3000 nm.

Figure 4B:
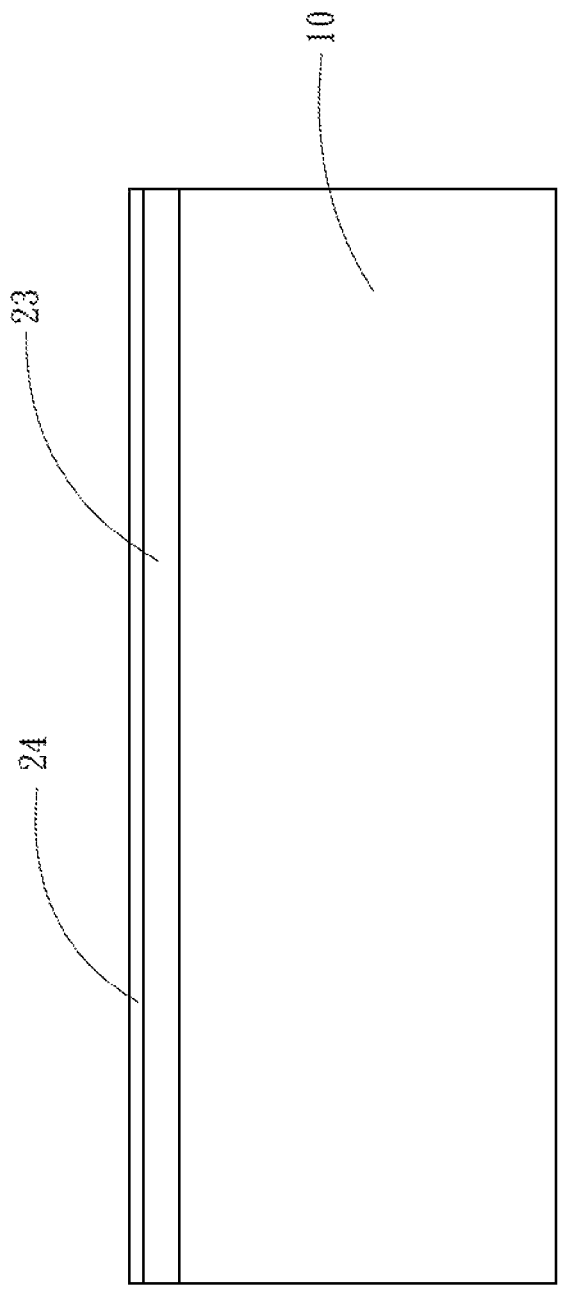

In the step S1B, form a second electrode layer 24 on one side of the first electrode layer 23, which is far away from the substrate 10, as shown in FIG. 4B, wherein the second electrode layer 24 is made of a material selected from the group consisting of gold, platinum, iridium, palladium, and combinations thereof, and wherein the second electrode layer 24 has a thickness of 10-1000 nm. As the second electrode layer 24 is to contact a tested material, the biological sensitivity of the second electrode layer 24 is higher than that of the first electrode layer 23. Thereby, the test accuracy can be increased. The second electrode layer 24 is made of more expensive material. Therefore, the electrode layer formed by the first electrode layer 23 and the second electrode layer 24 is cheaper than the electrode layer formed by merely the second electrode layer 24 for a given thickness. Hence, the embodiment using the first electrode layer 23 and the second electrode layer 24 can effectively reduce the cost. The second electrode layer 24 is formed on the first electrode layer 23 with an electroplating technology or a sputtering technology.

Figure 3:
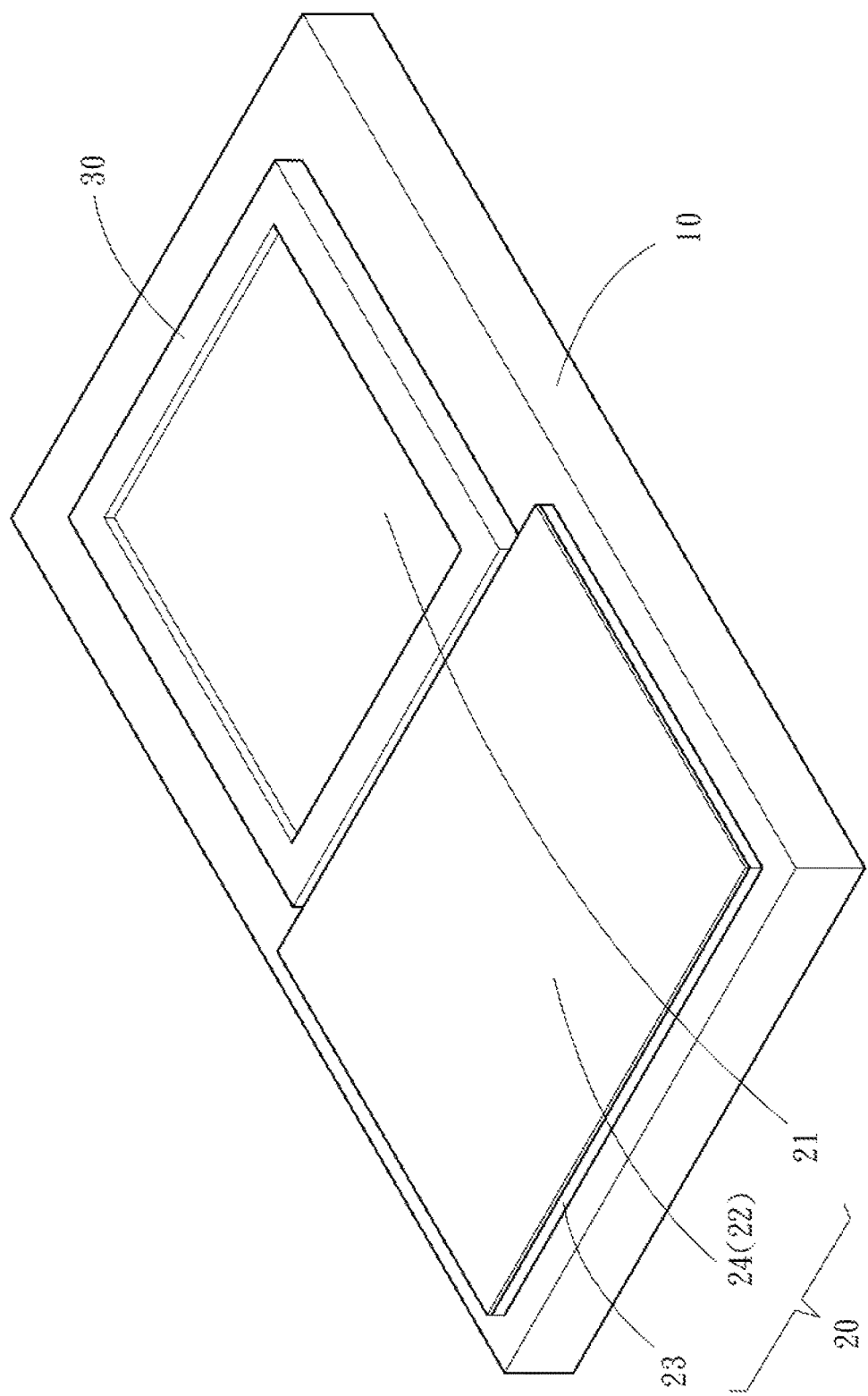
FIG. 3 is a perspective view schematically showing a portion of the structure of an electrochemical sensing test piece according to the first embodiment of the present invention.
Figure 4C:
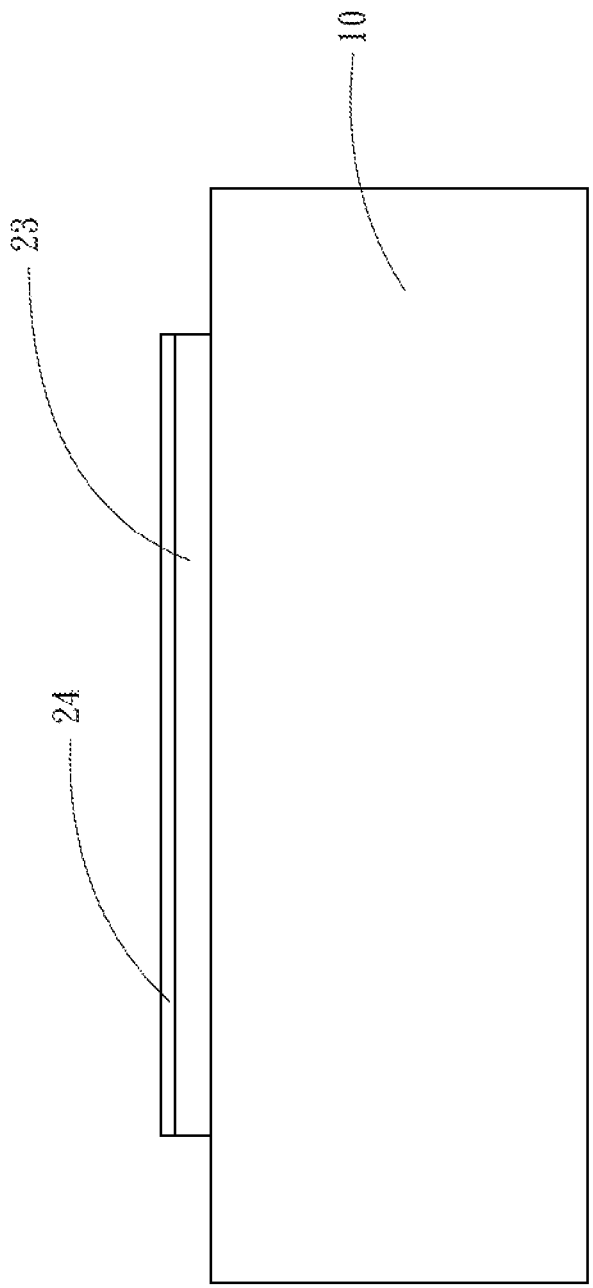

In the step S2, etch the electrode layer 20 to remove the perimeter of the electrode layer 20 and reduce the area of the electrode layer 20 to be smaller than the area of the substrate 10, as shown in FIG. 4C. The electrode layer 20 includes a test zone 21 to contact the tested material and a reading zone 22 neighboring the test zone 21 and read by an instrument (not shown in the drawings). In FIG. 3, the second electrode layer 24 is extended together from the test zone 21 to the reading zone 22. Since the reading zone 22 would not contact the tested material, thus in another embodiment, the second electrode layer 24 is only disposed on the test zone 21, and the reading zone 22 only disposes the first electrode layer 23 as the electrode. Thus, the cost can be further reduced.

Figure 4D:
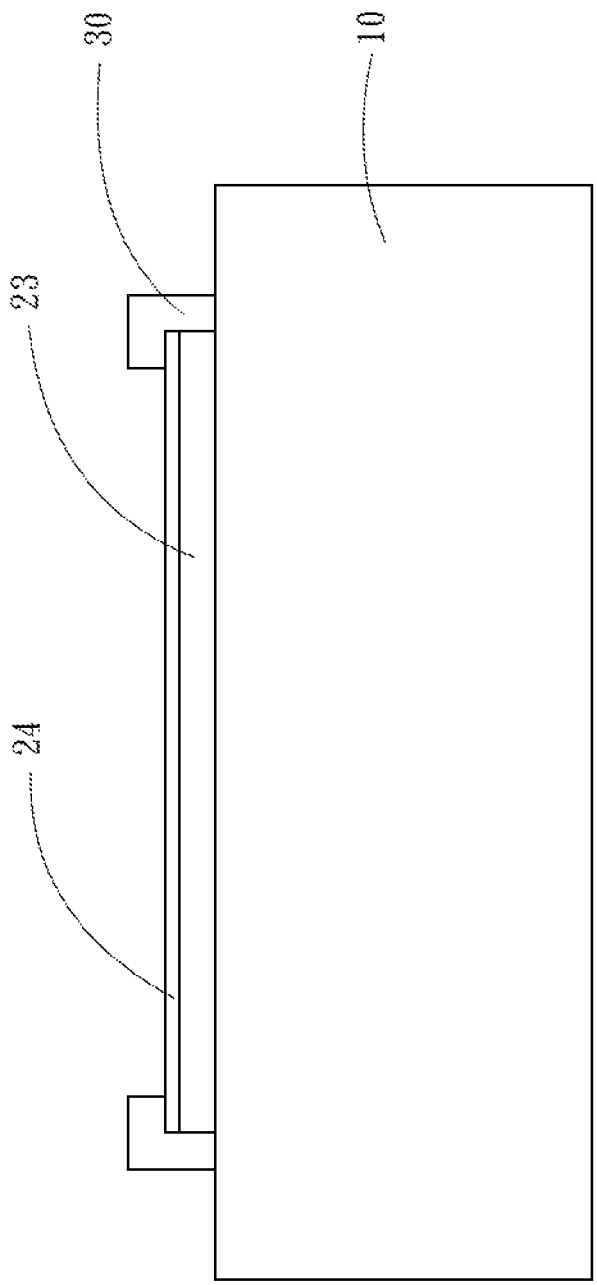

In the step S3, form an insulation member 30 surrounding the test zone 21 and covering the perimeter of the test zone 21, as shown in FIG. 3 and FIG. 4D. In one embodiment, the fabrication process of the insulation member 30 includes steps: forming the insulation member 30 around and on the test zone 21 of the electrode layer 20; and photolithographically etching a portion of the insulation member 30 that is formed on the test zone 21 to make the insulation member 30 only cover the perimeter of the test zone 21. However, the present invention is not limited by the embodiment. In one embodiment, the insulation member 30 is made of a material selected from the group consisting of insulating inks, photoresist compounds, dry-film photoresist compounds, and ultraviolet-curable inks.

Figure 4E:
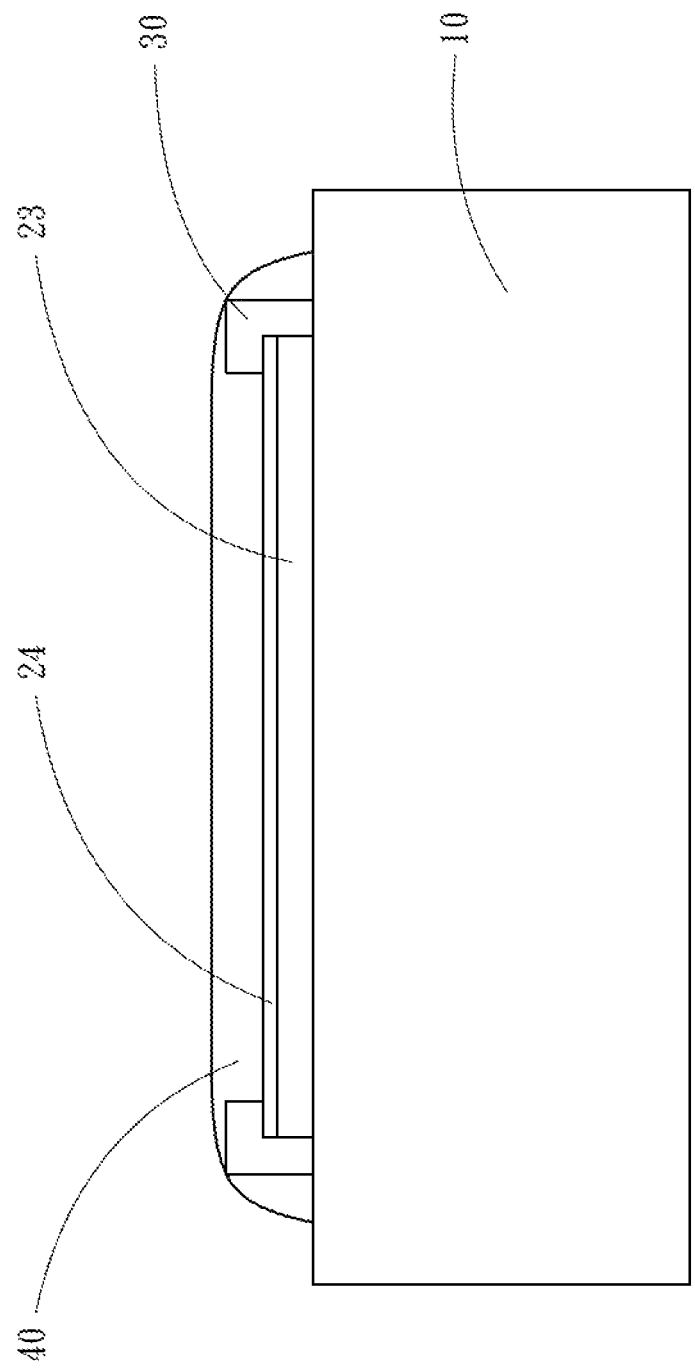

In the step S4, form an enzyme layer 40 on the test zone 21. As shown in FIG. 4E, a portion of the enzyme layer 40 may be distributed on the periphery of the insulation member 30.

Figure 4F:
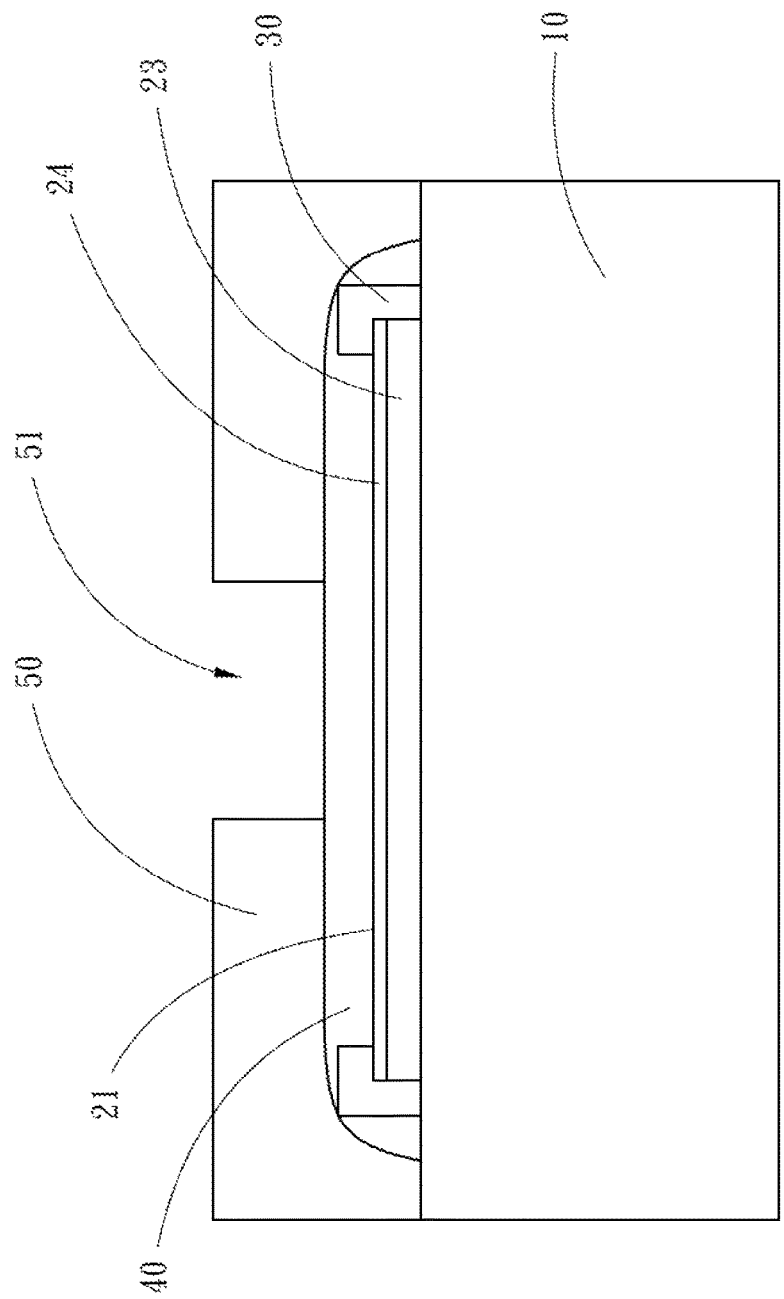

In the step S5, form an insulation layer 50 on the enzyme layer 40 and the periphery of the reading zone 22 and fabricate the insulation layer 50 to have an opening 51 revealing a portion of the enzyme layer 40, as shown in FIG. 4F. In one embodiment, the opening 51 is fabricated with a photolithographic etching technology. However, the present invention is not limited by the embodiment. In one embodiment, the insulation layer 50 is made of a material selected from a group including insulating inks, photoresist compounds, dry-film photoresist compounds, and ultraviolet-curable inks.

Figure 1:
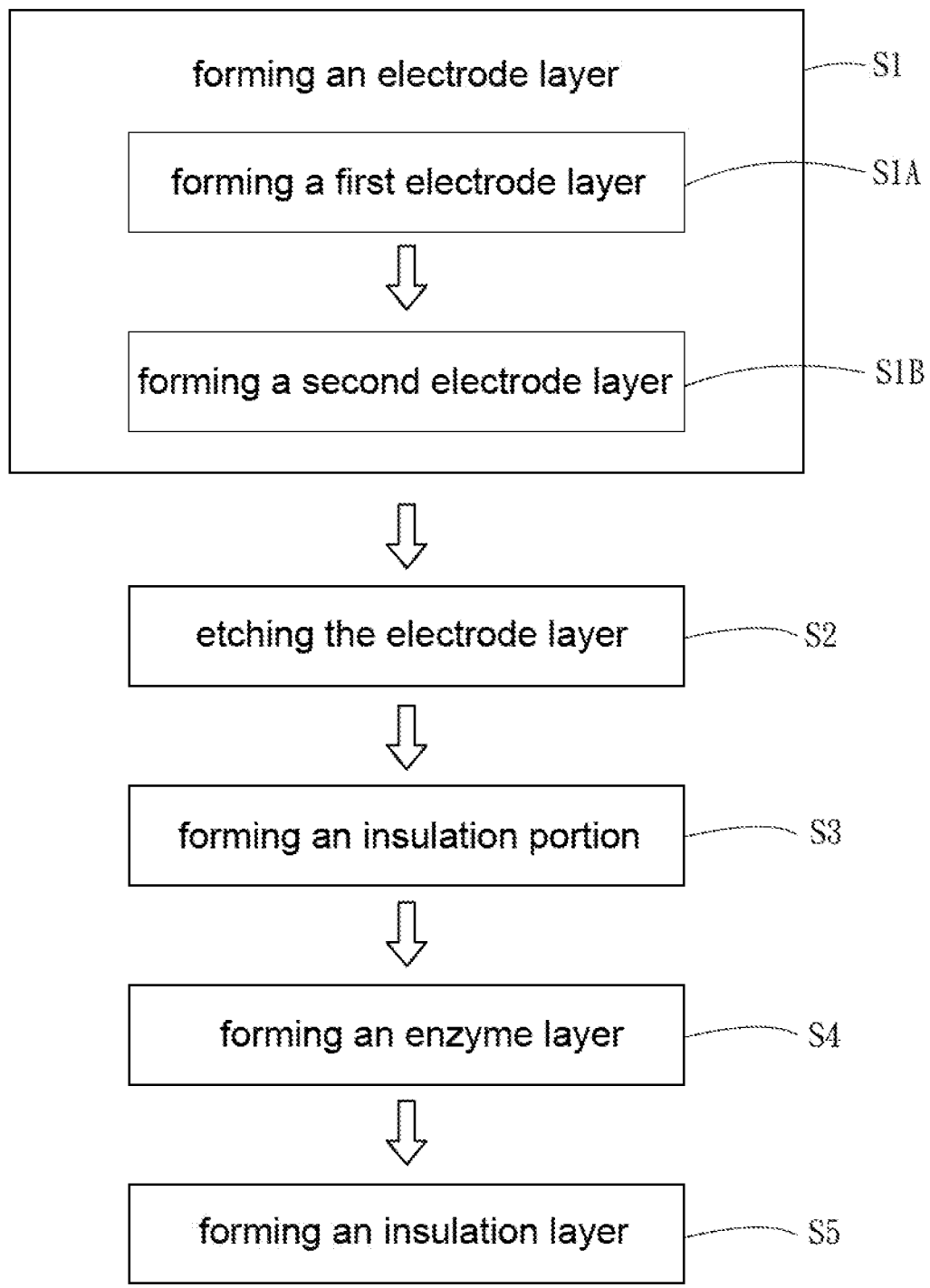
FIG. 1 is a flowchart of a method for fabricating an electrochemical sensing test piece according to a first embodiment of the present invention.
Figure 2A:
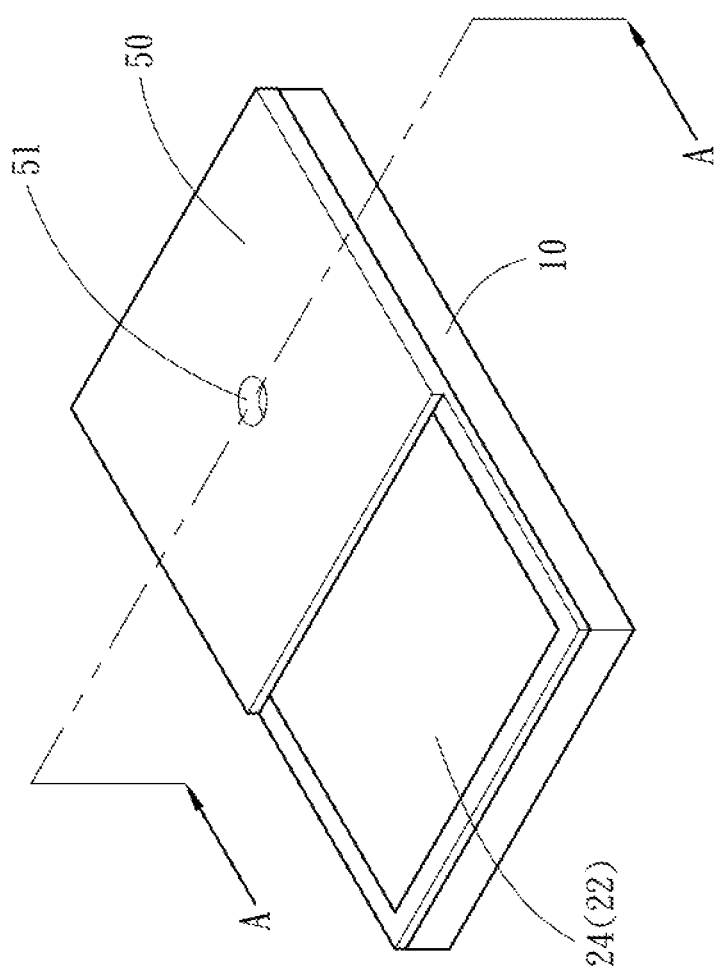
FIG. 2A is a perspective view schematically showing the structure of an electrochemical sensing test piece according to the first embodiment of the present invention.
Figure 2B:
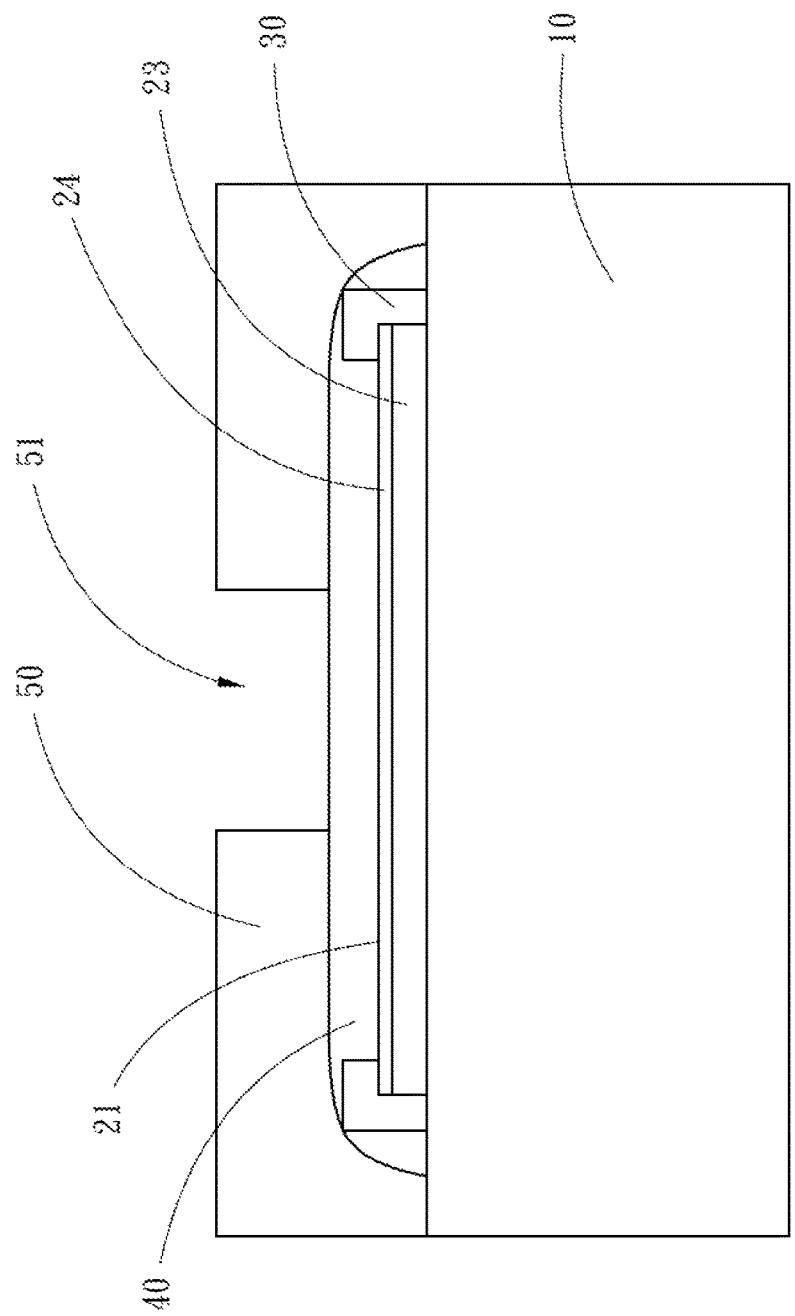
FIG. 2B is a sectional view taken along Line A-A in FIG. 2A.

After the test piece is completed according to the above-mentioned embodiment, the appearance thereof is like that shown in FIG. 2A. The sectional view taken along Line A-A in FIG. 2A is shown in FIG. 2B. While a test is to be undertaken, the tested material is filled into the opening 51 to contact the enzyme layer 40 and the test zone 21. Meanwhile, another electrochemical test piece is used as a reference electrode. Then, the test is started. As the insulation member 30 is disposed on the periphery of the electrode layer 20 and the perimeter of the test zone 21 of the electrode layer 20, the insulation member 30 not only can prevent the tested material from spreading to the reading zone 22 but also can fix the effective reaction area where the tested material contacts the test zone 21. Thus, the measurement accuracy is increased. Besides, the insulation member 30 and the insulation layer 50 can prevent the lateral sides of the electrode layer 20 from being exposed and thus exempt the lateral sides from contacting the external air, the tested material and the enzyme layer 40 lest the measurement precision be affected.

Figure 5:
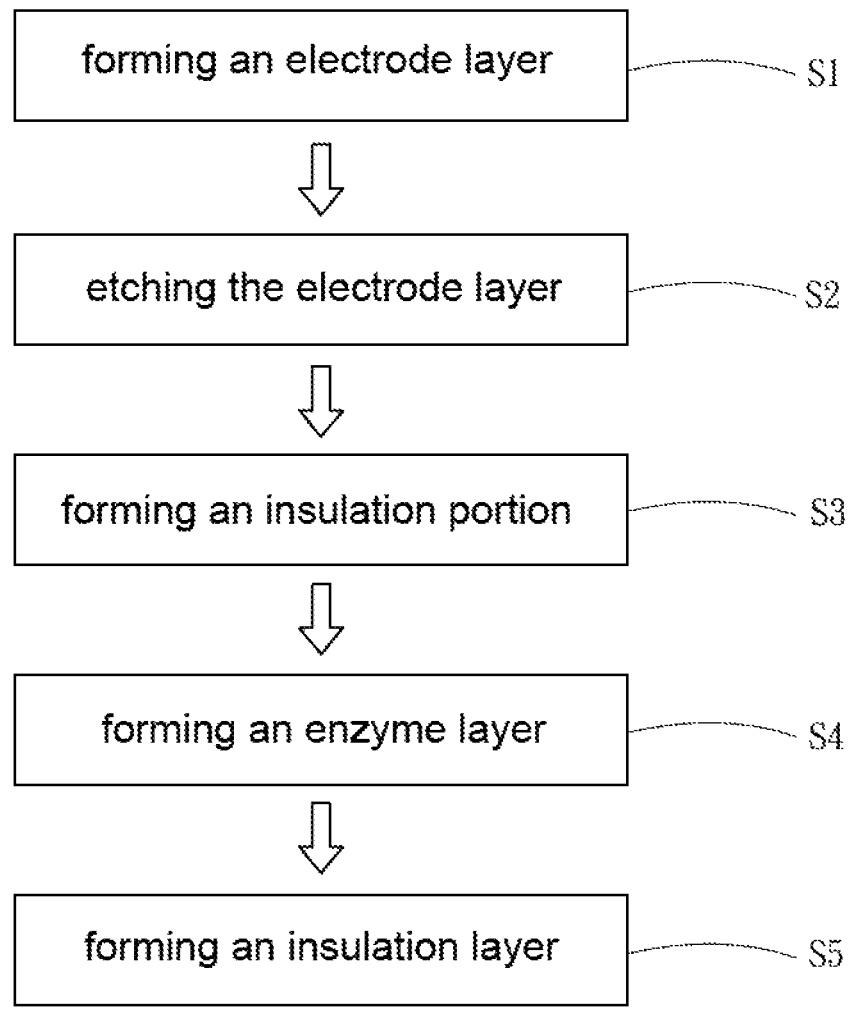
FIG. 5 is a flowchart of a method for fabricating an electrochemical sensing test piece according to a second embodiment of the present invention.

Refer to FIG. 5 for a second embodiment of the present invention. Compared with the first embodiment, the second embodiment does not involve the step S1A and the step S1B but forms an electrode layer 20 merely. Therefore, the second embodiment has lower fabrication complexity. In the second embodiment, the electrode layer 20 is made of a material selected from the group consisting of titanium, copper, nickel, silver, aluminum, chromium, gold, platinum, iridium, palladium, and combinations thereof.

In summary, the present invention is characterized in
1. Increasing the test accuracy via using the second electrode layer having a higher biological sensitivity to replace a portion of the first electrode layer, and decreasing the cost because only a portion of the first electrode layer is replaced by the second electrode layer having a higher price;
2. Fixing the effective reaction area of the tested material and the test zone and preventing the tested material from spreading to the reading zone via using a photolithographic etching technology to form the insulation member surrounding the test zone and covering the perimeter of the test zone, and thus upgrading test precision;
3. Preventing from exposure of the lateral sides of the electrode layer via disposing the insulation member and the insulation layer on the perimeter of the electrode layer, and thus exempting test accuracy from being degraded.

What is claimed is:

1. A method for fabricating an electrochemical sensing test piece, comprising the steps of:
    S1: forming an electrode layer on a substrate;
    S2: etching the electrode layer to remove a perimeter of the electrode layer and reduce area of the electrode layer to be smaller than area of the substrate, wherein the electrode layer includes a test zone and a reading zone neighboring the test zone;
    S3: forming an insulation member surrounding the test zone and covering a perimeter of the test zone;
    S4: forming an enzyme layer on the test zone; and
    S5: forming an insulation layer on the enzyme layer and a periphery of the reading zone and fabricating the insulation layer to have an opening revealing a portion of the enzyme layer.

2. The method for fabricating an electrochemical sensing test piece according to claim 1, wherein in the step S1, the substrate is made of a material selected from the group consisting of polyethylene terephthalate (PET), polyethylene naphthalate (PEN), cellulose triacetate, polylactic acid, and combinations thereof.

3. The method for fabricating an electrochemical sensing test piece according to claim 1, wherein in the step S1, the electrode layer is made of a material selected from the group consisting of titanium, copper, nickel, silver, aluminum, chromium, gold, platinum, iridium, palladium, and combinations thereof.

4. The method for fabricating an electrochemical sensing test piece according to claim 1, wherein in the step S3, the insulation member is made of a material selected from the group consisting of insulating inks, photoresist compounds, dry-film photoresist compounds, and ultraviolet-curable inks.

5. The method for fabricating an electrochemical sensing test piece according to claim 1, wherein in the step S3, the insulation member is fabricated with a photolithographic etching technology.

6. The method for fabricating an electrochemical sensing test piece according to claim 1, wherein in the step S5, the insulation layer is made of a material selected from the group consisting of insulating inks, photoresist compounds, dry-film photoresist compounds, and ultraviolet-curable inks.

7. The method for fabricating an electrochemical sensing test piece according to claim 1, wherein the step S1 further comprises the steps of:
 S1A: forming a first electrode layer on the substrate; and
 S1B: forming a second electrode layer on one side of the first electrode layer, which is opposite to the substrate, to stack the first electrode layer and the second electrode layer to form the electrode layer.

8. The method for fabricating an electrochemical sensing test piece according to claim 7, wherein in the step S1A, the first electrode layer is made of a material selected from the group consisting of titanium, copper, nickel, silver, aluminum, chromium, and combinations thereof, and wherein in the step S1B, the second electrode layer is made of a material selected from the group consisting of gold, platinum, iridium, palladium, and combinations thereof, and wherein the second electrode layer has a higher biological sensitivity than the first electrode layer.

9. The method for fabricating an electrochemical sensing test piece according to claim 7, wherein in the step S1A, the first electrode layer has a thickness of 20-3000 nm, and wherein in the step S1B, the second electrode layer has a thickness of 10-1000 nm.

* * * * *